United States Patent [19]

Paules

[11] Patent Number: 4,711,687
[45] Date of Patent: Dec. 8, 1987

[54] METHOD OF USING PRECISION CAN LABELER WITH OPTIONAL TAX STAMP APPLICATOR

[75] Inventor: Eugene H. Paules, Huntington, Conn.

[73] Assignee: United States Tobacco Company, Greenwich, Conn.

[21] Appl. No.: 930,343

[22] Filed: Nov. 12, 1986

Related U.S. Application Data

[62] Division of Ser. No. 820,940, Jan. 21, 1986, Pat. No. 4,657,622.

[51] Int. Cl.4 .......................... B44C 1/17; B44C 1/00
[52] U.S. Cl. .................................. 156/235; 156/238; 156/542; 156/DIG. 10; 156/DIG. 27
[58] Field of Search ............... 156/230, 238, 240, 249, 156/297, 235, 361, 351, 540, 541, 542, 362, 336, DIG. 4, DIG. 8, DIG. 9, DIG. 10, DIG. 11, DIG. 12, DIG. 27, DIG. 33; 198/416, 409, 408, 402

[56] References Cited

U.S. PATENT DOCUMENTS

| | | | |
|---|---|---|---|
| 2,602,561 | 7/1952 | Carter | 156/DIG. 27 |
| 3,738,888 | 6/1973 | Williams | 156/541 |
| 3,992,244 | 11/1976 | Craig et al. | 156/541 |
| 4,086,744 | 5/1978 | Seragnoli | 198/416 |
| 4,181,561 | 1/1980 | Seragnoli | 156/DIG. 4 |
| 4,217,164 | 8/1980 | La Mers | 156/DIG. 33 |
| 4,303,461 | 12/1981 | La Mers | 156/361 |
| 4,338,152 | 7/1982 | Del Bianco et al. | 156/361 |
| 4,397,710 | 8/1983 | Gaylord | 156/DIG. 27 |
| 4,601,771 | 7/1986 | Wesley | 156/361 |

Primary Examiner—Donald E. Czaja
Assistant Examiner—Louis Falasco
Attorney, Agent, or Firm—Fred A. Keire

[57] ABSTRACT

A method for precision labeling of containers such as cans for labeling top, bottom or sides, including labeling sides of containers with lids; side labels may have secondary labels, e.g., tax stamps, placed thereon.

2 Claims, 17 Drawing Figures

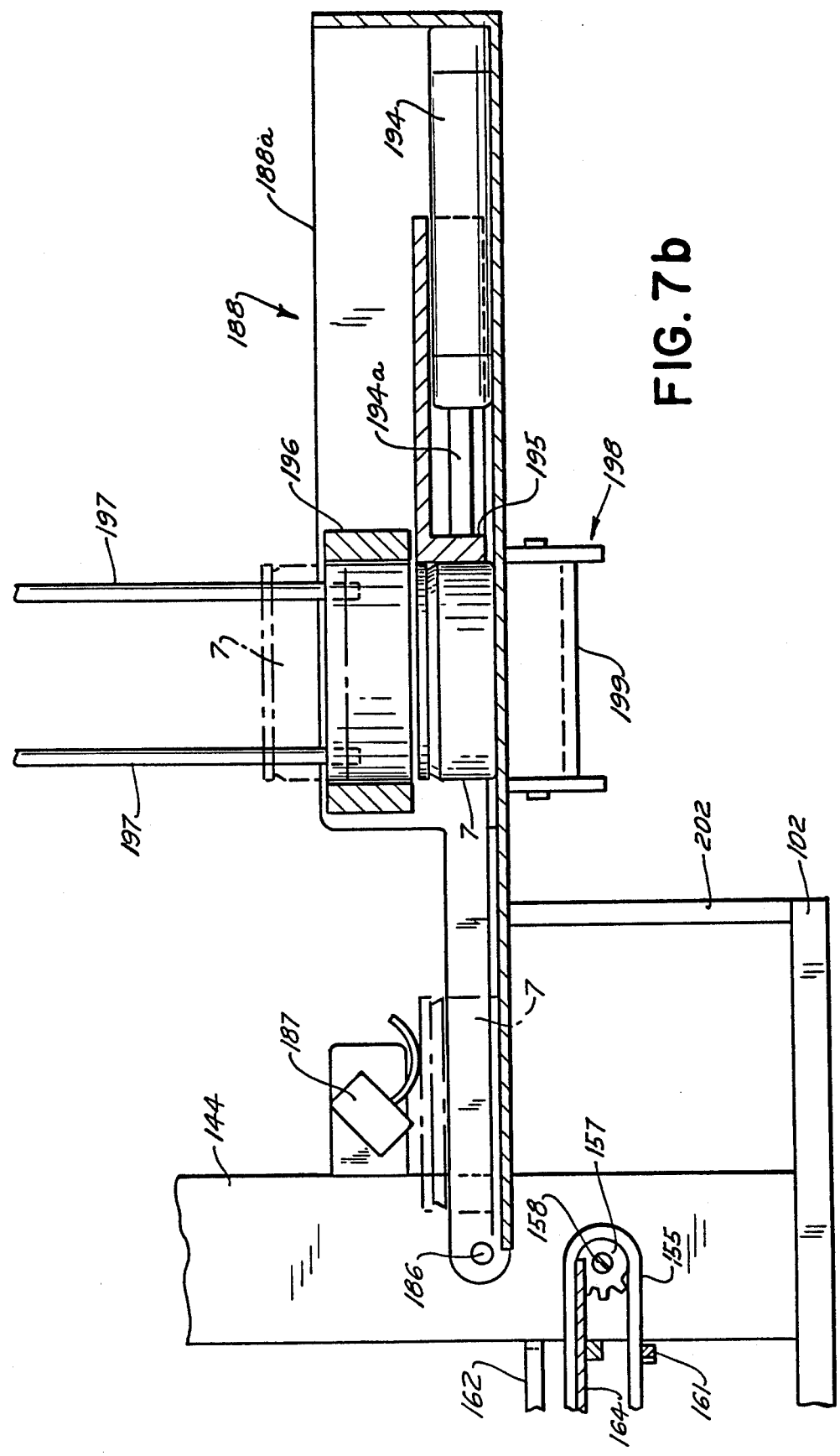

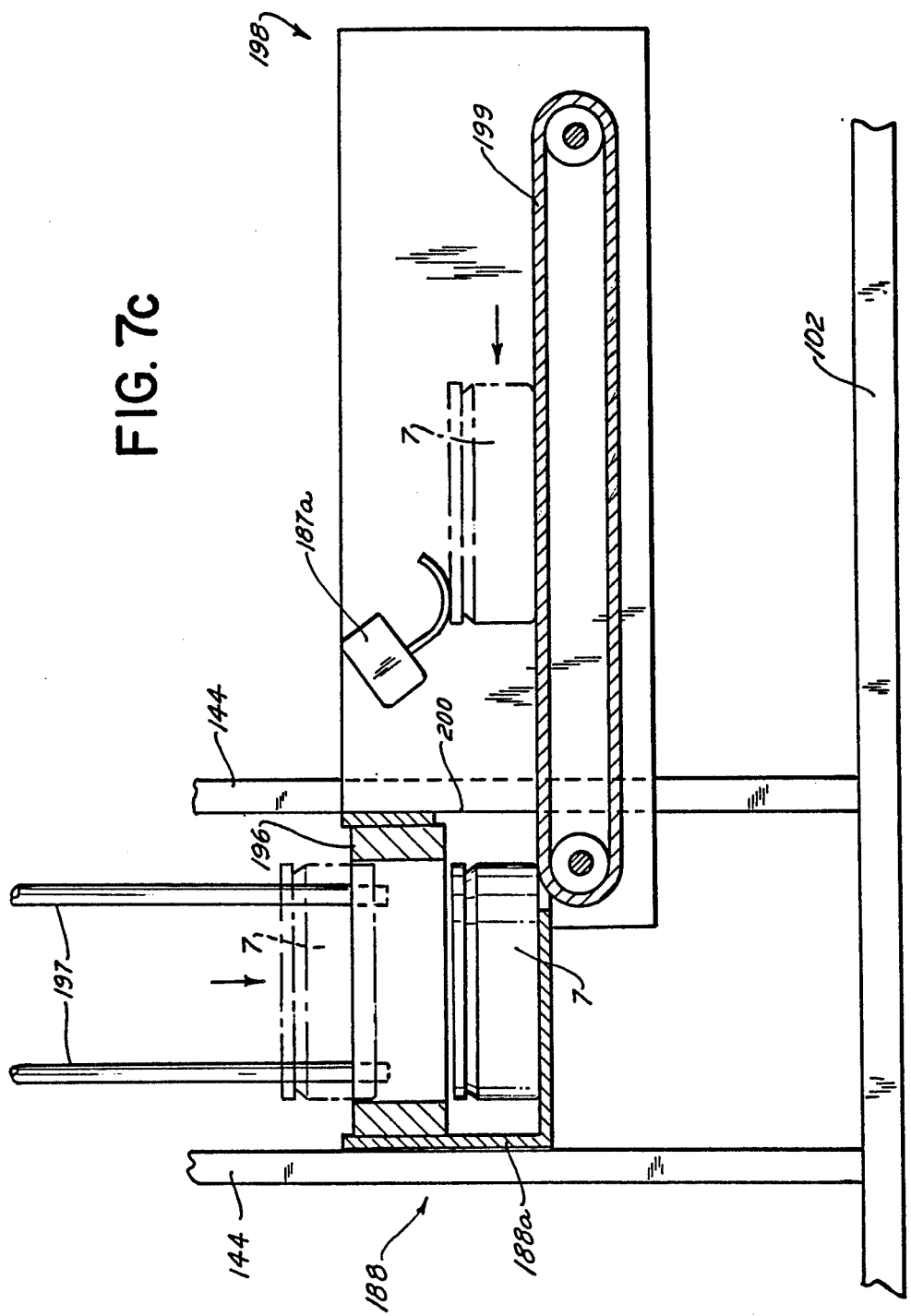

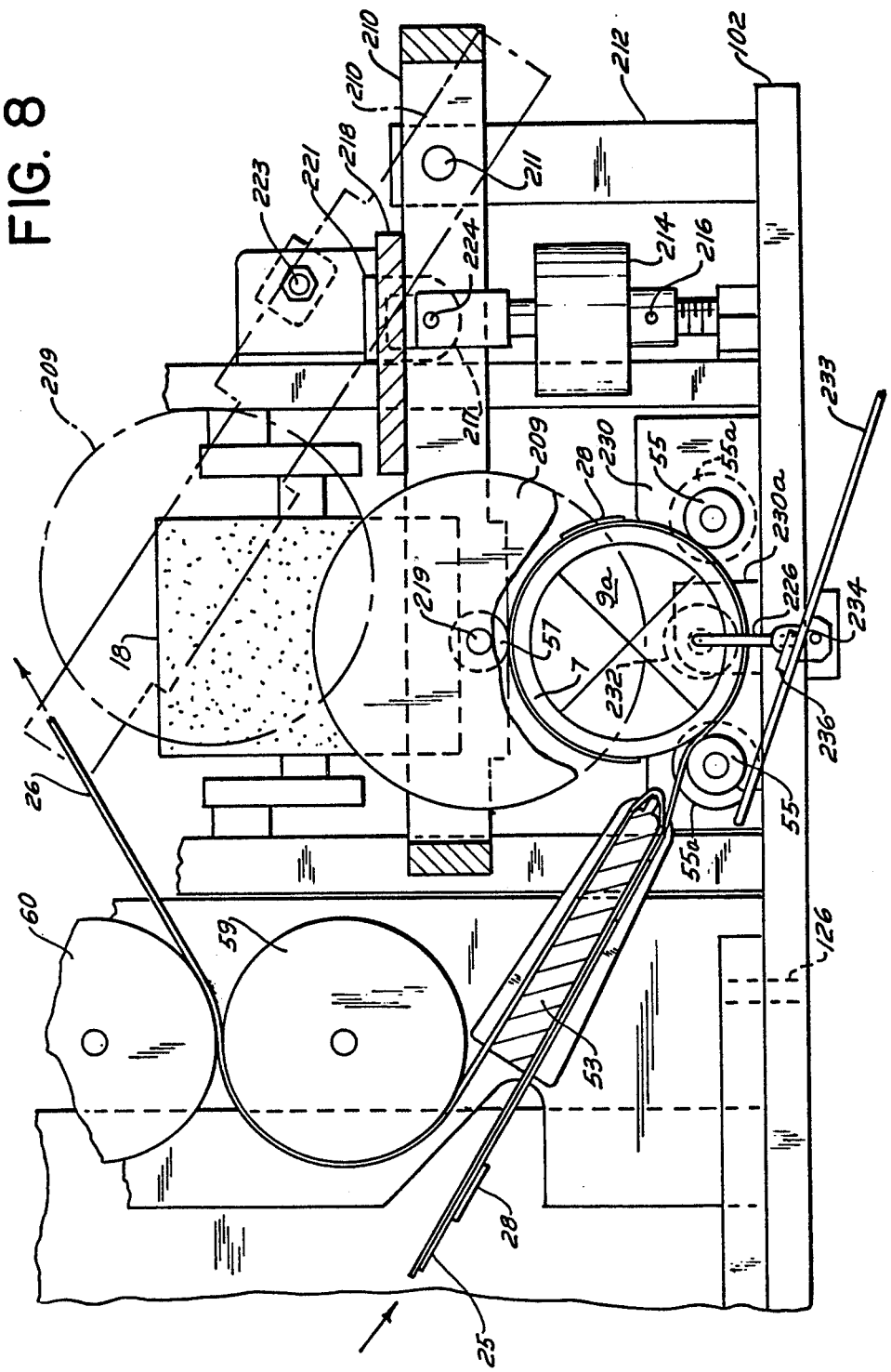

METHOD OF USING PRECISION CAN LABELER WITH OPTIONAL TAX STAMP APPLICATOR

This application is a division of application Ser. No. 06/820,940, filed Jan. 21, 1986, now U.S. Pat. No. 4,657,622.

INTRODUCTION

This invention relates to a machine and a method for application of labels to containers; more specifically, this invention relates to a machine for applying a top label to a container such as a circular top label. Further, this invention relates to the application to the same container of a side label with a secondary label on top thereto such as a tax stamp optionally applied to the label.

More particularly, this invention relates to a machine for a precise, repeatable application of a top, bottom and/or side label with precisely positioned secondary label, e.g., tax stamp for a side label, or even top or bottom label at any designated position for the tax stamp and associated high quality control features relating thereto.

BACKGROUND FOR THE INVENTION

For containers which have large diameter to height ratios, considerable commercial information is carried on the top label. If the container, moreover, has a lid which is removable and in use replaceable, the container has a lid slightly larger in diameter than the container itself. For containers where the contents may be repeatedly used in small portions, it is also essential that the container be sealed for freshness and that the state of the label indicates that no one has tampered with the contents before its purchase.

In some jurisdictions, containers having controlled goods, such as smokeless tobacco, certain candies containing alcohol or even controlled substances such as prescription drugs must carry additional information on the top, bottom or side lahel. Often this information is in the form of tax stamps or additional stamps of approval of one sort or another. These secondary labels, which for ease of communication are called "tax stamps", are not necessarily used for all the goods being made by the same manufacturer.

Still further, additional information may be placed on the containers and thus the bottom of the container often serves for the purpose of affixing a label as the commercial information normally has taken up the entire top area for the container as well as the sides of it.

In labeling these containers, it is also essential that the information be precisely positioned and not be easily removable from the containers so that in the transportation and display of the goods, the labels may not fall off or be torn off by improper placement and/or location.

Still further, taxing authorities jealously guard the placement of the tax stamps in their proper location, as well as carefully monitor that the tax stamps are indeed placed on each and every container. Thus the controlled substance or medication containing containers must at all times carry this tax or other information and at all times must convey to the governmental authorities that the proper information is on the label or a tribute has been paid to the government. Failure of proper affixation or failure to have the required information on the label may result in fines or other penalties. Therefore, a machine which applies these stamps on the container must operate with extreme accountability and precision.

BRIEF DESCRIPTION OF PRIOR ART

In an industrial setting, the machines which fill the container are not necessarily coupled to a labeling machine. Typically, for top labeling an independently situated and operated labelinq machine sequentially applies to a previously filled container a top label to it. Thereafter, the top labeled goods are removed from the top labeling machine and placed on trays or like means for transporting the containers to a machine which, in turn, then applied the side label. There is considerable inefficiency in the stacking and restacking of the containers after each of the operations. Loading and reloading of these containers, either for further workup or for placing a tax stamp thereon, are time consuming, labor inefficient operations.

In a typical ooeration, because of the high degree of assurance needed to verify the presence of tax stamps, tax stamp application is often a labor-intensive or even a manual labor operation. When applying tax stamps to the side label, these stamps are often very imprecisely placed and therefore create an unsightly appearance to the goods.

Prior art labeling machines, such as top label machines which are often conveyor belt operated, have the label application position signalled by a can or a container activating a switch when the container advances in the labeling zone. The signaling, however, is done typically with microswitches or switches, and these have considerable hysteresis.

Further, in prior art machines conveyor operation is also imprecise as the load on the conveyor often indicates or causes the machine to operate with different torque characteristics. These problems cause the container to move at an unpredictable rate in an imprecise manner through the label application zone. As a consequence, label placement and can location is often not synchronous and results in failure to apply a label precisely or even miss the top section of the container and apply the label overhangingly on one or more sides. Because the labels are typically in modern applications self-adhesive (without independent glue application), the labels may be removed even in the machine by stripping these from the container or in transportation or even in further operation such as when the side labels are placed thereon. Also the overhung portions of the label may be torn off and may thus impair the proper operation of the machine to where failure results.

Another problem which has befallen the prior art machines and which is even more serious is the misaliqnment of the side labels when these are placed on containers. This is especially true for containers which have a lid fitted on top of the container or can. A lid, in order to fit on the container, invariably has a slightly larger diameter than the container body itself. As a result of the differences in the diameter, a label which is placed on the container by the rotational application of the label, will misalign to where the trailing end of the label is considerably displaced from the leading edge of the label. Although overlapped, these labels often cause the ends either to protrude above or below the container or the information which must be read across the label is misaligned and difficult to follow.

Still further, because of the difference in container diameter and the difference in application, the self-adhesive labels will have imprecise and buckling portion or a wrinkled appearance. This appearance causes some of the containers to be improperly sealed and the purchaser to question the product's freshness or integrity. Moreover, it is difficult to detect tampering with a wrinkled side label, and therefore product appeal is considerably diminished when the labeling appearance is inferior.

BRIEF DESCRIPTION OF THE INVENTION

The present invention is to a machine which has a precise top label operation to wherein the adjustment of the top label may be within a few thousands of an inch as regards its placement, and the precise adjustment is repeatable without substantial machine drift or accumulated machine error. Further, the present machine includes in combination a top label feeding section which presents a container for labeling to the machine with alternative feed means. The machine may be coupled to various other machines in which the containers are filled, providing independent manufacturing centers. Thus an entire manufacturing capability no longer need be devoted to a single product being produced and then labeled, but various machines may be operated, producing different products with different labels.

The present machine further allows the top label placement without control hysteresis found in prior art machines such as based on on-off switches and torque drift shown by conveyors used for labeling.

Still further, the present machine in the top laheling operation provides another alternative in that the bottom labeling may also be accomplished in the same machine.

Still further, as part of the same machine but after the completion of the top labeling, appropriate side labeling by the same machine accomplishes precise sealing, substantially eliminating misalignment of the side label and thus the side seal. It is now possible to achieve a placement on the can of a side label of a very neat appearance with great precision. Moreover, "tax stamp" placement on the side label may also be disabled if tax stamp placement is unnecessary. This disablement may be accomplished without impairinq the automatic cycling of the machine and the automatic top and side labeling process.

Still further, a tax stamp placement may be precisely controlled and tax stamps cut to a size which suit the particular label, all within precisely defined limits.

Further, in conjunction with the side labeling, the quality control aspects allow the rejection of improperly deposited tax stamps or labels without tax stamps. Thus, the reliability of the tax stamp labeling is superior to the best quality control features heretofore achieved by any machines known to the inventors.

In addition, the presently disclosed machine and the method for depositing the top and side labels are through precise gearing and clutch brake control means without the use of belts and belt-driven drives so that switch hysteresis, including contact bounce problems, no longer affect the quality or accumulate errors in the machine in its operation.

As a further benefit of the presently disclosed machine, it has an efficiency in output at least twice compared to the output of the best prior art labelers known to the inventors.

Still further, as mentioned before, the machine may be coupled with various other machines which are used for making and/or filling containers in such a manner that no conveying and/or independent stacking of the goods are necessary, and considerable manufacturing flexibility may be achieved. Thus when each unit is operating independently of any other units, manufacturing vulnerability has been considerably decreased as compared to the prior art labeler. Hence, the present machine allows substantial manufacturing invulnerability with cycle times which are considerably faster based on products originating from a coupled feed source or independent feed source as need arises.

DETAILED DESCRIPTION AND DRAWINGS THEREFOR

With reference to the drawings in which the present invention is illustrated and wherein the various aspects of the invention have been schematically set forth, and wherein:

FIGS. 7a to 7c are various views of the additional means for feeding the machine illustrated in FIG. 7;

FIG. 8 is a side view along lines 8—8 of FIG. 6 of the side label placement section in an enlarged section;

Figure 1:
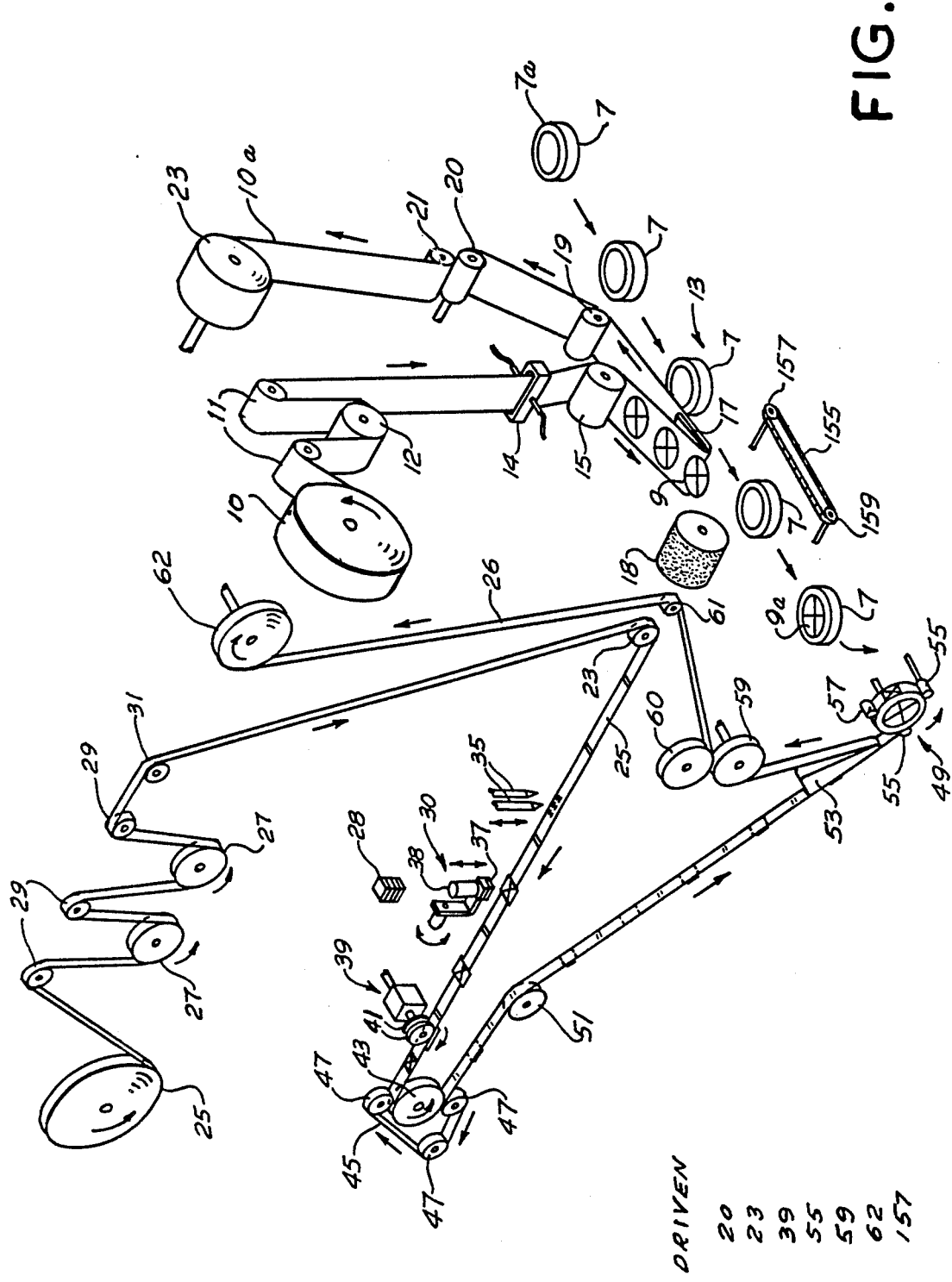
FIG. 1 is an overall schematic representation of the process train for the top label and side label placement.

Returning now to FIG. 1 showing schematically the top and side labeling process, in FIG. 1, on the right hand side a can 7 on which a top label 9 is to be placed has a can lid identified as 7a. An indentation for receiving the top label 9 is shown as 9a. The top label 9 is carried on a top label carrier strip 10a, and the top label carrier strip 10a free of labels has been shown on the top right hand side of FIG. 1. The top label supply is on a reel 10 carrying at precise locations self-adhesive labels 9. The top label carrier strip 10a is a release agent coated paper strip. The supply reel 10 thus contains the top labels 9 precisely positioned on the carrier strip 10a; from this reel, the carrier strip 10a is played around an appropriate idler pulley 11 and around a feed speed compensation wheel 12, and a further idler pulley 11, through a top label detection bracket 14. In FIG. 1, a top label applicator section has been identified as 13.

Top label stripper feed wheel 15, for stripper 17, guides the top labels 9 into the stripper plate 17 for stripping the labels 9 from the top label carrier strip 10a. A label press down wheel 18 assures the proper adhesion of the top label 9 on a can 7.

The can with the label is then ready to he sent on to the side label application section identified as 49 in FIG. 1.

The top label carrier strip 10a is guided from the top label application section by carrier removal pin 19 around which the top label carrier strip 10a is being removed by the carrier driven roller 20. The carrier drive roller 20 has a complementary engagement roller 21 which assures a positive movement for the top label carrier strip 10a, and a carrier strip takeup reel 23 is also driven to assure proper takeup of the top label carrier strip 10a.

Turning now to the side lahel application, a side label 24 has been illustrated on the side label carrier 26. The side label supply spool has been shown as 25 on top of the left side of FIG. 1. Thereafter the side label supply spool is unwound by leading the side label carrier 26 around idler pulleys 29 and side label speed compensation wheels 27.

The carrier 26 is guided to the tax stamp application section 30 by side label pre-feed wheel 31, the side label feed wheel being identified as 33.

Figure 3:
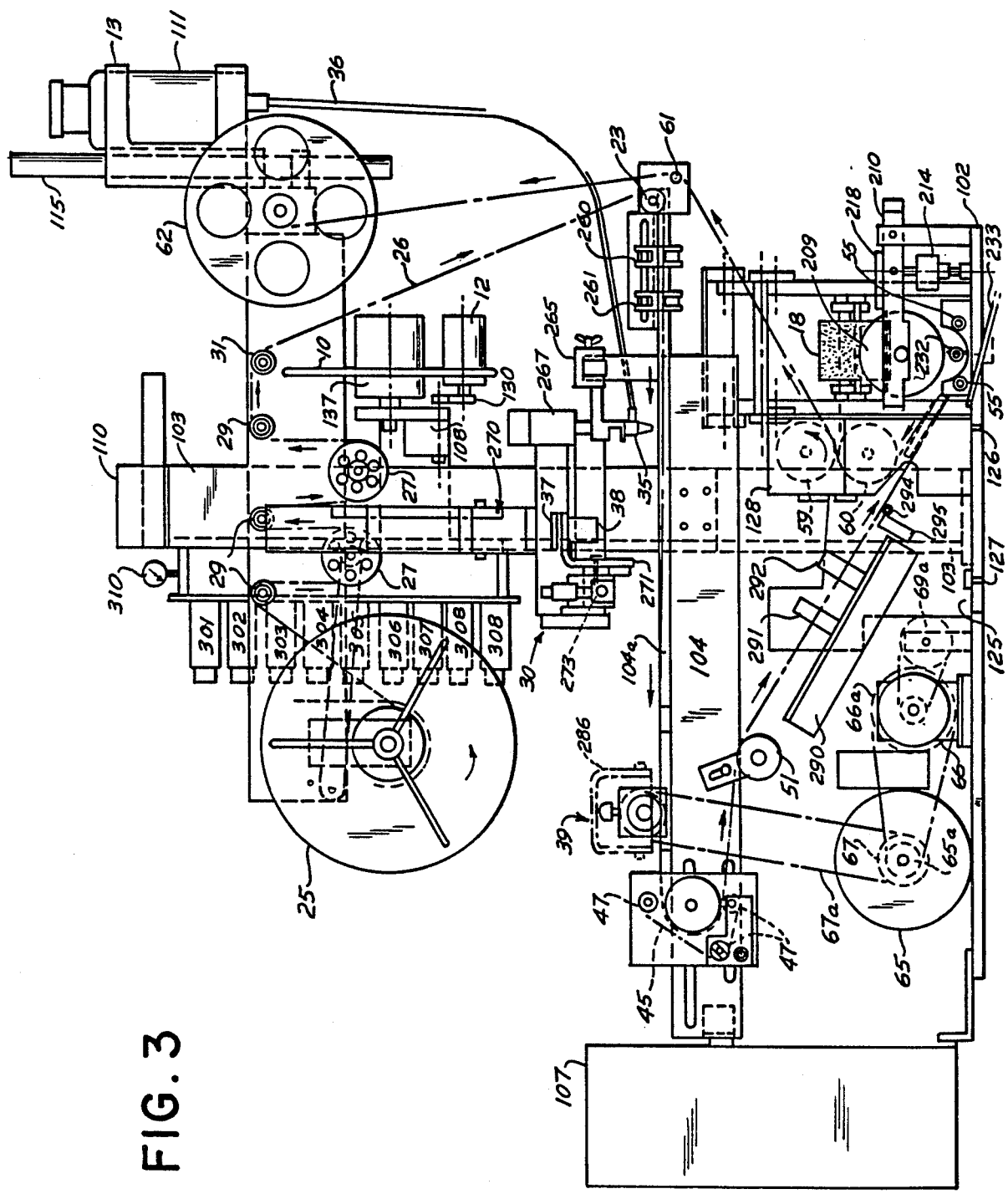
FIG. 3 is a side elevation illustrating the tax stamp placement and the side label application.

The glue applicator 35 for the tax stamp placement has the gluer supply lines 36 lead to it. These are not shown in FIG. 1, but are shown in FIG. 3. The tax stamp pickup and deposit head is shown as 37. The reciprocating pneumatic cylinder 38 is used for the tax stamp pickup and deposit head 37. Tax stamps 28 have been identified as being stacked in a magazine which will be further described herein. Item 39 identifies tax stamp slitter section and 41 a pair of tax stamp slitter knives straddling the side label 24.

A side label tax stamp takeoff wheel 43 is shown as being used in conjunction with press down belt conveyor 45 for securing tax stamp 28 on the side label 24. The press down belt conveyor 45 is driven by the side label 24 and side label carrier 26 through tax stamp press down conveyor belt pulleys 47, three of which have been shown in FIG. 1.

From there the side label carrier 26 with the side labels 24 carrying the tax stamp thereon are guided by wheel 51 into side label applicator section 49. This section consists of side label stripper plate 53 from which the side labels 24 are stripped from the carrier 26, the carrier 26 being driven by the side label carrier drive wheel 59 in combination with side label driven wheel 60.

A pair of can rotation driven rollers 55 are used in combination with label press down roller 57 for application of the side label 24 (with or without the tax stamp thereon). The carrier takeup guide pulley 61 guides carrier 26 into side label carrier takeup spool 62.

The above-described top and side label schematic process train illustrates schematically the application sections, i.e., the various sections in which the labels are being applied to the container. A further description of these sections will be by reference to the other drawings as the details in the schematic have been purposely omitted to make for easy understanding of the present machine and the method for application of the labels on the containers.

Figure 2:
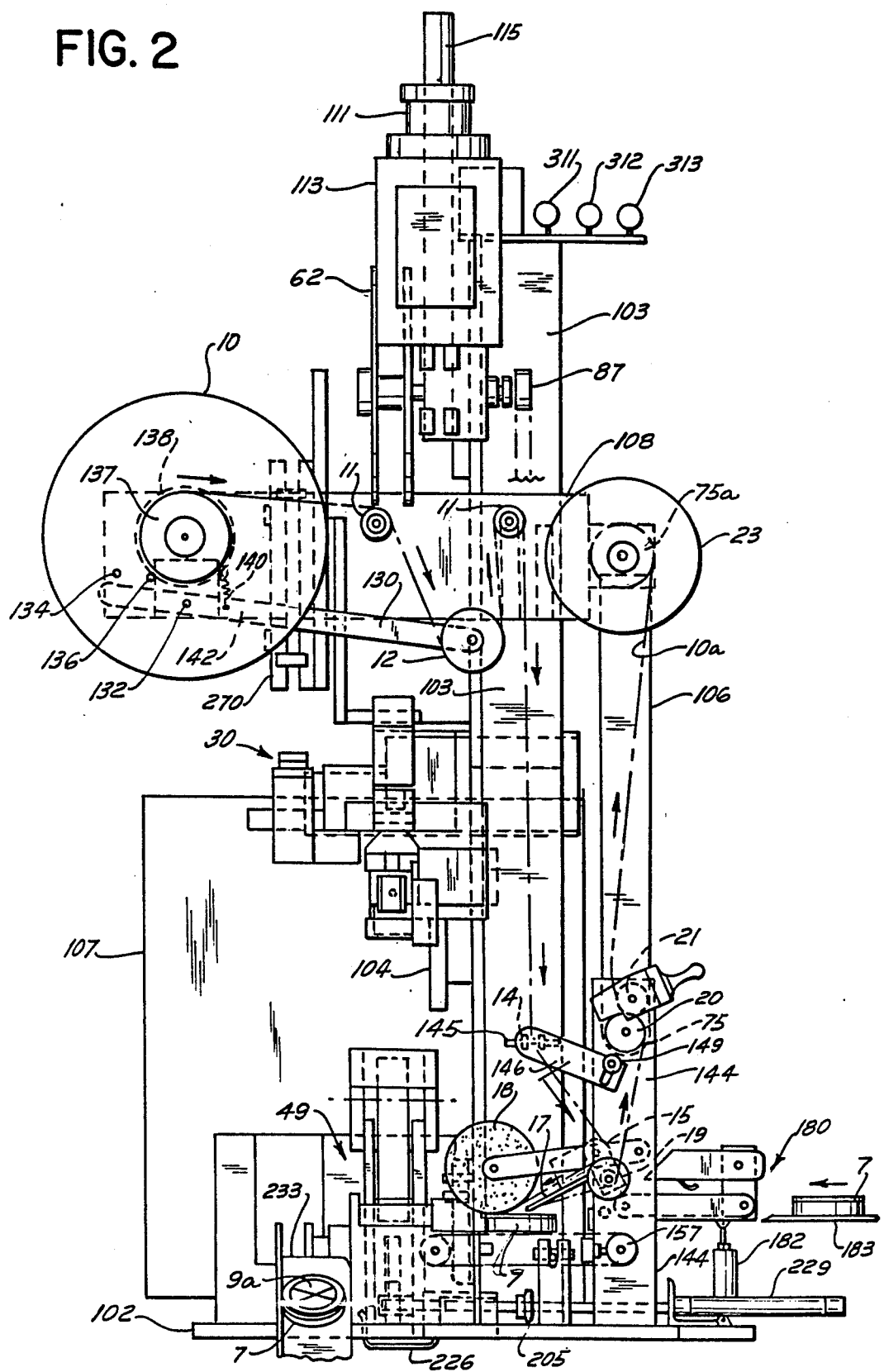
FIG. 2 is a front elevation of the machine illustrating the top label placement.

Before turning to FIG. 2 which illustrates in front elevation the top label 9 application, it should be worthwhile to review the drive train employed for the various interrelated drive sections driven elements shown also in tabular form in FIG. 1a.

Figure 4:
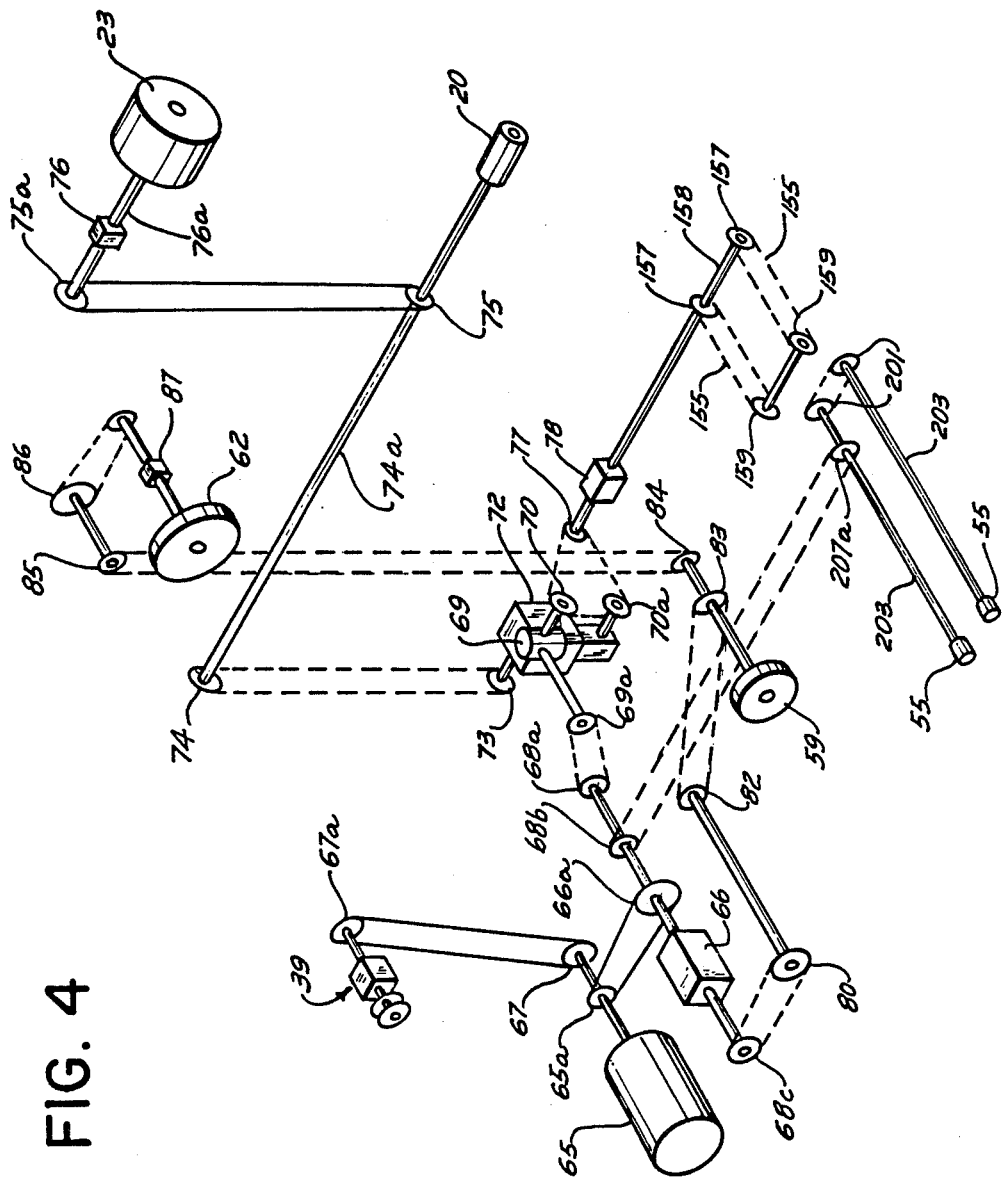
FIG. 4 is a schematic illustration of a single motor, synchronous drive used for achieving position drift-free label placement.

Thus turning now to FIG. 4, the motor for driving the entire machine is illustrated as 65; it may be a one quarter horsepower motor rated about 3 to 5 amperes. Motor 65 drives a pulley 65a by means of a gear belt (not shown), driving a brake-clutch control device 66 through the brake-clutch pulley 66b.

Directly off the motor is a tax stamp slitter knife pulley 67 driving a pulley belt 67a for the slitter knives 41. For ease of understanding, the chain belts have not been shown, but their interconnections have been mentioned.

Sprocket wheel 69a, driven by a chain (not identified), drives a right angle drive 69. Sprocket wheel 68b is interconnected to a pair of can rotation wheels 55 and side label carrier drive wheel 59 as will be further described herein.

Side label carrier 26 is driven by wheel 59, which is achieved through the sprocket wheel 68c, again as it will be further described herein.

Thus turning first to the right angle drive 69, it is interconnected (by a chain) to the sprocket wheel 66a of the brake-clutch control 66. From the right angle drive 69, the takeoff sprocket wheels 70 are interconnected to a sprocket drive wheel 71 for brake-clutch control device 72 for top label carrier drive roller 20 and the takeup reel 23 for top label carrier strip 10a. Accordingly, the brake-clutch control 72, for the top label carrier drive roller 20 and for top label carrier takeup reel 23 are interconnected through a chain sprocket 73 to a chain sprocket wheel 74, and these in turn interconnect with the driven roller 20, through a sprocket shaft 74a. On shaft 74a is identified a pulley wheel 75 which is coupled to the side label carrier strip takeup reel 23 through a complementary pulley 75a. A mechanical slip clutch 76 is placed on a common shaft 76a for the top label carrier takeup reel 23.

Figure 5:
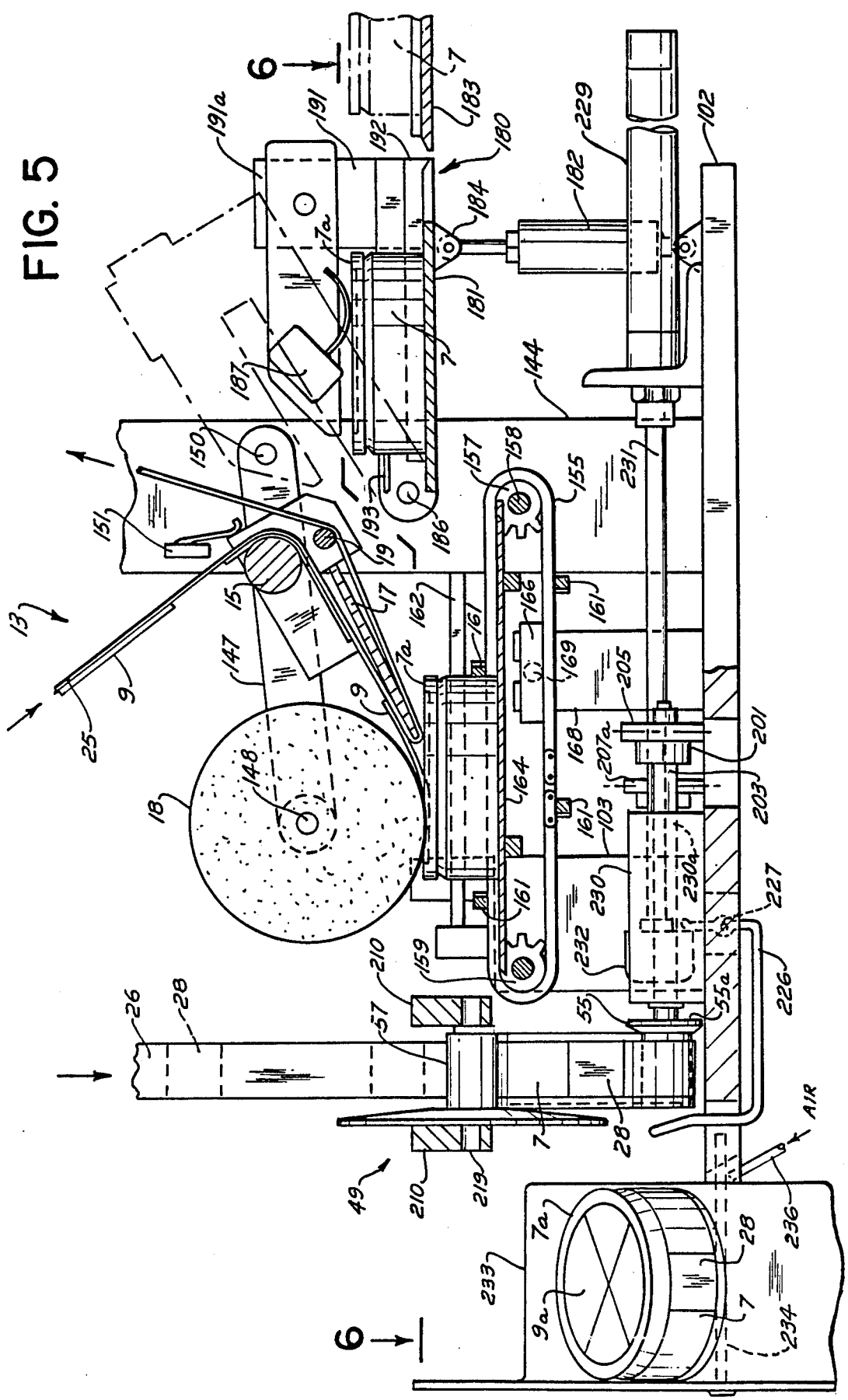
FIG. 5 is a fragmentary side elevation in an enlarged section illustrating the top label application.

The second of a pair of the sprocket wheels coming off right angle drive 69 is shown as 70a and is interconnected to a sprocket drive wheel 77 for a brake-clutch control device 78 for the chain conveyor 155 as will be further discussed herein in connection with the top labeler section 13 shown in FIG. 5.

With reference to the side label carrier 26 drive train, the drive sprocket 80 for driving a shaft 81 and sprocket wheel 82 is interconnected to the side label carrier drive wheel 59 for driving the side label carrier 26 through the sprocket wheels 82 and 83. In turn, side label carrier drive wheel 59 is further interconnected with a pair of sprocket wheels 84 for driving through drive trains 85 and 86 side label carrier takeup spool 62 with a mechanical brake-clutch mechanism 87 therefor.

For the can rotation drive rollers 55, sprocket wheel 68b is taken directly from the brake-clutch control device 66 through an idler 207 through to a sprocket wheel 207a which drives one of the shafts 203 for the can rotation driven rollers 55. A takeoff sprocket wheel 201 on the same shaft 203 as sprocket wheel 207a, via a chain, rotates via sprocket 201 the other can rotation drive roller 55.

The above explanation of the drive train thus completes the description of the interconnection of the various devices. These are driven by one motor, and the interrelationship of these is through chain driven devices or gear belts. Hence, there is no slippage, but there is a completely synchronous relationship whenever the various drive trains are being activated simultaneously or sequentially (including the commonly driven elements for each).

As seen in FIG. 4, the can rotation drive rollers 55 are continuously rotating; this also holds for the right angle drive 69, because these two are interconnected without any brake-clutch control devices such as 66, 72 or 78.

Similarly, the slitter knives 41 are continuously rotating as the drive for these is taken off directly from the motor 65.

The brake clutch control devices 66, 77 or 78 are those typically available in the industry and are solenoid operated. A convenient source for these is Warner Electric Brake and Clutch Company, South Beloit, Ill., 61080. The right angle drive 69 is a 2:1 reduction drive and is available such as from Hubb City Engineering, P.O. Box 1089, Aberdeen, S.D., 57401.

For a can of 2.562 inches in diameter with a height of 0.9375 inches through the right angle drive 69, the conveyor speed for the chain conveyor 155 is 5.750 inches per second, which is also the same as for the top label drive roller 20 speed which is driving the carrier strip 10a at 5.750 inches per second. However, because of the considerably longer side label drive, the side label drive roller 59 has a 2.625 inches diameter, giving a circumference of 8.246 inches. The top label drive roller 20, however, has a diameter of 0.718 inches, giving a circumference of 2.255 inches.

The above illustrations are only to show an embodiment used with the machine, but are not necessarily restrictive as the machine is capable of applying different top and side labels to the same container. However, the gearing or timing devices for the different cans and labels, respectively, would be appropriately modified to provide the necessary differences in the top label and side label lengths and thus drive duration.

Turning now to FIG. 2, it shows in front elevation the machine and illustrates further the top label application section shown as 13 in the drawing. In further detail, the machine base plate has been shown as 102, the main horizontal frame member as 104, and the main vertical frame member as 103. The housing for the electronic and electrical control means for the instruments and for the sensors has been shown as 107 in FIGS. 2 and 3. Bracket 108 has been shown for locating top label supply reel 10 and top label carrier strip takeup reel 23. In conjunction with FIG. 3, bracket 105 for holding side label supply spool 25 and side label speed compensator idler pulleys 29, and side label carrier takeup spool 62 have been shown in FIG. 3.

The switches, such as a machine or component on-off switch panel, have been shown as 110 for the machine, e.g., for the top label section 13 as well as for the side label section 49 and tax stamp section 30.

Turning now back to FIG. 2, glue container 111 is held in a bracket 113. The bracket 113 is mounted on post 115 which is appended to the main side label supply bracket 105.

In turn, the bracket 105 has been attached to main vertical machine member 103.

The top label supply reel 10 has a dance arm 130 which at the end thereof has the feed speed compensator wheel 12. The dance arm 130 has a pivot point 132 and a detent pin 134 for it. A brake band 138, with a brake band anchor pin 136, is mounted on bracket 108 circumferentially around an inner hub 137. The brake band 138 via spring 140 is attached to the dance arm at anchor point 142. The purpose for the dance arm is as follows: as the driven wheel 20 takes up the carrier belt strip 10a, the dance arm is lifted and it releases the brake band 138, allowing the label to be advanced. However, because of the size, the mass and different circumferential speed as the top label supply is being exhausted (as well as the mass being varied), the dance arm 130 prevents excessive override of the top label supply wheel 10 and thus imprecise positioning of the labels. Thus the reel 10 which is mounted on the inner hub 137 is substantially stopped whenever the carrier strip advance is stopped.

The weight of the dance arm 130 thus effectively acts as a brake, as well as a speed compensator, based on the advance of the top label carrier strip 10a. Top label idler pulley 11 thus allows the dance arm to be maintained within given limits with the detent pin 134 preventing the shock loading of the system as the top label supply reel 10 is being depleted.

As the label is advanced downwardly, it passes through top label eye bracket 14 which is mounted between a pair of adjustable holding posts 146 mounted on a pair of posts 144 between which the drive roller 20 is mounted.

A photoelectric sensor eye 145 (preferably infrared) thus detects the trailing edge of a top label and three labels downstream it controls by electronic control means, which will be further explained herein, the positioning of the top label for a precise placement of the top label on a container.

From the photoelectric sensor eye 145, the top labels 9 on the carrier strip 10a advance through the stripper feed wheel 15 into the stripper 17. The label press down wheel 18 is attached via its two pivot arms 147 at the pivot points 150 on the pair of posts 144. The shaft 148 for the press down wheel 18 has been identified in FIG. 2.

The adjustment for the sensor eye bracket posts 146 is by a pair of adjustment screws 149.

Although, as indicated above, one of the adjustments may be mechanical, further adjustments are also available such as via the control means, for example, delay circuits, electronic timing means, etc., which are well known in the art.

In order to illustrate the top label application section in greater detail, that is, section 13, FIG. 5 shows an enlarged view of this section shown in FIG. 2. Thus the location of the stripper plate 17 is shown with respect to the can. The stripper plate 17 attached to stripper plate bracket 17a is also pivoted around stripper post 19. Stripper plate bracket 17a and thus the stripper 17 attached thereto are adjustable vernier-like in a cross-direction by a pair of threaded positioning knobs (not shown) on each side of a pair of posts 144. Further, the preceding sequence also alerts the operator via a horn (not shown) turning on a light (not shown), and causes the incoming containers to be label bypassed until the corrective action is taken. Stripper plate bracket 17a cams a normally closed switch 151 open to activate a circuit and cause feed bridge 180 to be raised by air cylinder 182 and prevent the top label to be advanced in the event of a can jam.

Cans 7 are being fed in a position using a feed bridge section identified as 180. The feed bridge 180 is mounted via pivot points 186 on the pair of posts 144.

If a can 7 has been properly detected on the conveyor by a sensor (not shown in FIG. 5, but shown in FIG. 6 as 163), the can 7 is then advanced to a can feed position by the can positioning chain conveyor 155. The conveyor 155 has in a cross-direction, that is, across the conveyor, an appropriate number of can positioning bars 161. These bars 161 are attached to the conveyor chain 155 and push forwardly can 7 in a very precise relationship. A label 9 advances simultaneously (with a slight delay, if necessary, for a lid rim if such is present) as previously discussed in connection with FIG. 4 and the drive train for this machine. Accordingly, the synchronously driven conveyor chain 155 advances with the synchronously interrelated drive wheel 20 taking away top label carrier strip 10a. The chain conveyor has a pair of idle sprocket wheels 159 around which the conveyor chain 155 is rotating. The shaft for idle sprocket wheels has been identified as 159.

Figure 6:
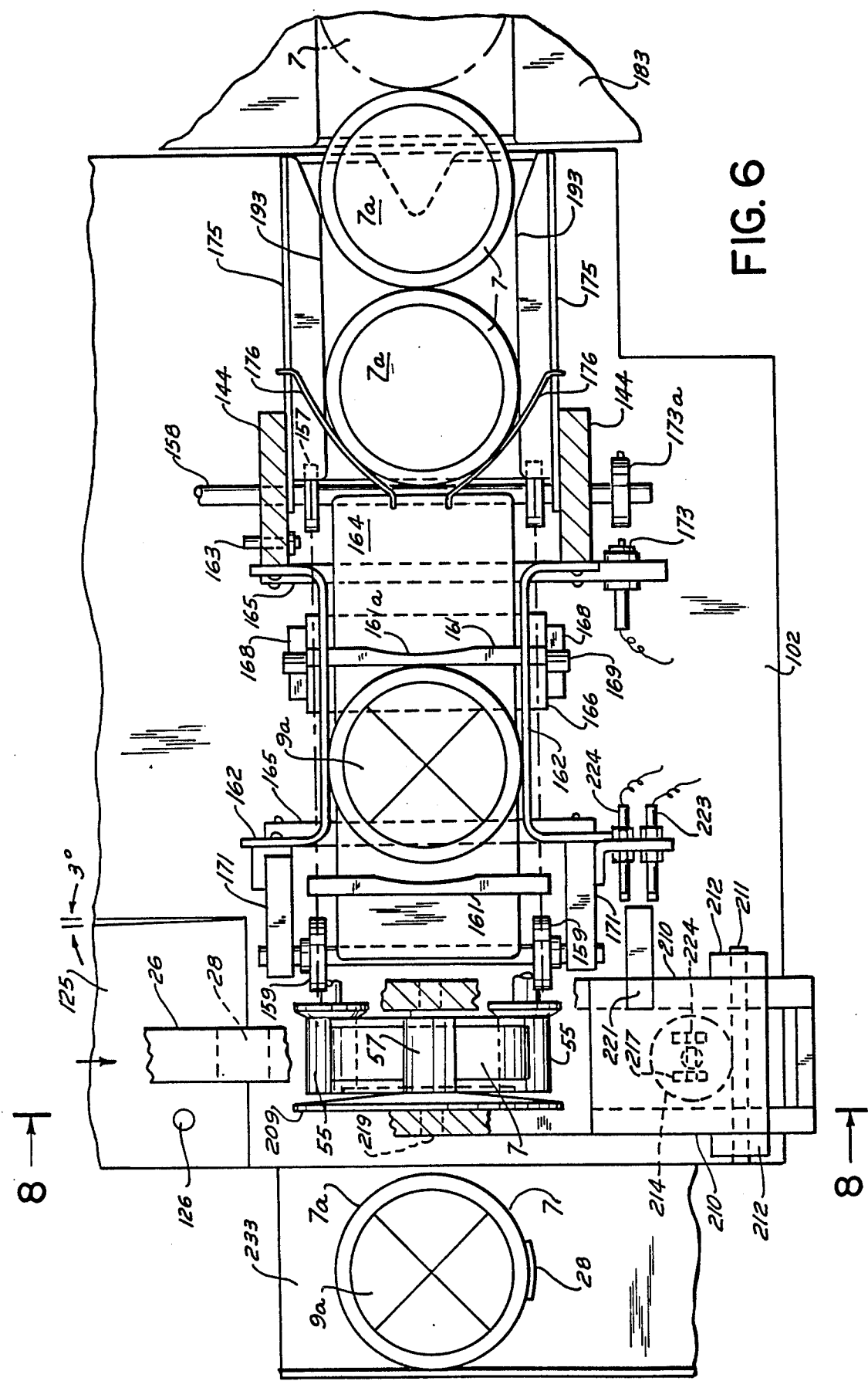
FIG. 6 is an enlarged fragmentary top view of the top and side label placement along lines 6—6 of FIG. 5.

A pair of can side guide bars 162 is also shown in FIG. 6, only one of which has been shown in FIG. 5. A label press down wheel 18 is typically of a foam material. When it is pivoting around press down wheel shaft 148, it bears down on the label and firmly causes the self-adhesive backed label to attach securely to can 7 at the indentation point 9a on the can 7. A pivot arm 147 for the press down wheel 18 may be spring loaded to bear down on the label 9, or it may be merely weighted down to accomplish its function.

A floating block 166 such as made of Teflon and the like is mounted on a shaft 169 and is restrained in a notch 169a on a post 168. The floating block 166 may be continuous from one side of the conveyor to the other, or it may consist of a pair of floating blocks 166. Block 166 acts as a conveyor chain 155 tensioner. Because of the limited space, a floating block has been employed, although other means, e.g., an idler wheel, may be used to accomplish this purpose. The function of the floating block 166 is to remove any error which may occur due to the chain tension variations.

FIG. 6 shows in top view the top label application section 13 shown in FIG. 5, and these two sections in conjunction thus illustrate the operation of the conveyor and also partially the side label section 49.

As the idle wheels 159 for conveyor chain 155 are mounted on a pair of bracket posts 171, the shaft 160 is precisely located vis-a-vis the complementary drive sprocket wheels 157 and the shaft therefor 158.

In FIG. 6, the chain conveyor can slide 164 is a polished plate such as of stainless steel. It is a smooth plate and can be made of other materials such as a Teflon sheet and the like. Slide 164 rests on cross posts 165 which are attached to a pair of posts 171 for idle sprocket wheels 159 and has another pair of posts 144 at the other end of the conveyor 155.

As shown in FIG. 6, a can 7 is moved along chain conveyor on chain conveyor can slide 164 by can positioning bar 161. However, the initial placement of the can is in the indentation 161a and is precisely located in a position relative to the label which will be advanced across the stripper plate 17. Indentation 161a for can 7 is shown in FIG. 6. As the can 7 is pushed precisely in the indentation guided by side guide bars 162, the precise positioning of the can is thereby achieved. The means for advancing the cans into the indentation 161a will be further discussed above.

As the can is placed on the can slide 164, a sensor 163 detects its presence and by appropriately interrelated means, such as a drive means for the conveyor 155 previously discussed starts the conveyor drive. For a container where the label is away from the edge, simultaneously with starting conveyor 155 drive, an appropriately predetermined millisecond timer is activated. When the can 7 has moved the predetermined distance (as calculated by the timer), the label carrier drive wheel 20 is started.

Can 7 and label 9 move in synchronization until photoelectric sensor 14 in FIG. 2 detects three labels upstream, and the trailing edge of a label thus stops the label drive. The conveyor 155 continues until proximity sensor 173 detects the actuator 173a. This indicates one shaft revolution or one compartment travel. This stops the conveyor 155 drive.

On the bridge deck 181 there are mounted bottom and top can side guides 192 and 193, respectively. The side walls 175 for the bridge deck 181 have attached thereto finger springs 176 which restrain the can from moving into position unless it is being urged forwardly by means which will be further discussed herein.

Returning to FIG. 5 and the bridge 180 consisting of the bridge deck 181 for the can feed, it has a pneumatic cylinder 182 for lifting the bridge 180 and thereby preventing a further feed from entering the bridge deck 181 from feed chute, conveyor, etc., 183, in the event the switch 151 shows a malfunction due to amming of the cans. The bridge 180 is pivoted around pivot point 186 for the same. The switch 187 is a normally open on-off switch and detects the presence or absence of a lid. If a can 7 enters the bridge 181 without a lid in place, this will stop the entire machine, alert the operator, raise the bridge 181 and bypass the incoming product.

As the bridge 180 is also provided with a bottom guide 192 and a top guide 193, it thereby defines a channel for advancing the cans from a feed chute 183 or a like conveyor stack feeder. A feed means arrangement has also been shown in FIGS. 7 to 7c which may be connected directly to the feed section 13 by utilizing the pivot points 186. This section has been identified as 188 and is an illustration of the previously mentioned feed means such as a feed chute, conveyor, stack feeder and the like means.

Figure 7:
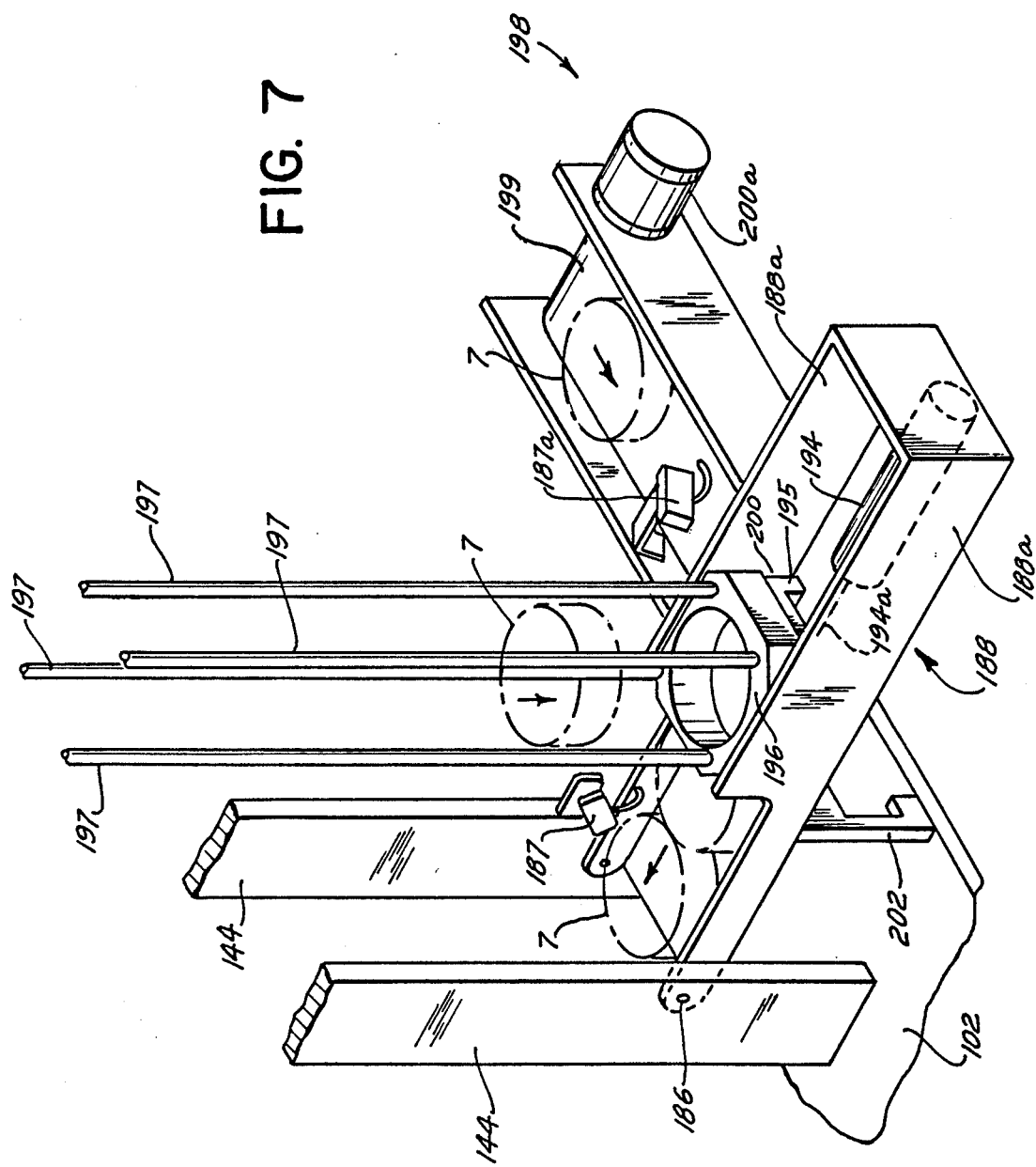
FIG. 7 is an illustration in a perspective view of an additional means for feeding the machine, not connected to a particular source but connected to the labeler illustrated in FIGS. 5 and 6.

The feed means 188 shown in FIGS. 7 to 7c thus consist of a channel defined by a three sides 188a and a pneumatic feed cylinder 194 for advancing can 7 from a feed stacker 196 base having four stacker rods 197. A feed head 195 is being driven by the pneumatic feed cylinder 194, the feed head being activated by the feed cylinder rod 194a. Feed head 195 thus reciprocates back and forth when the can drops in the circular opening of the can feeder stack base 196. Thus the can feeder base 196 serves also as a feed head 195 housing, and in this mode the cans which had a missing label or which need additional labeling put on the bottom thereof may be re-fed into the machine in a very convenient and facile manner.

Figure 7A:
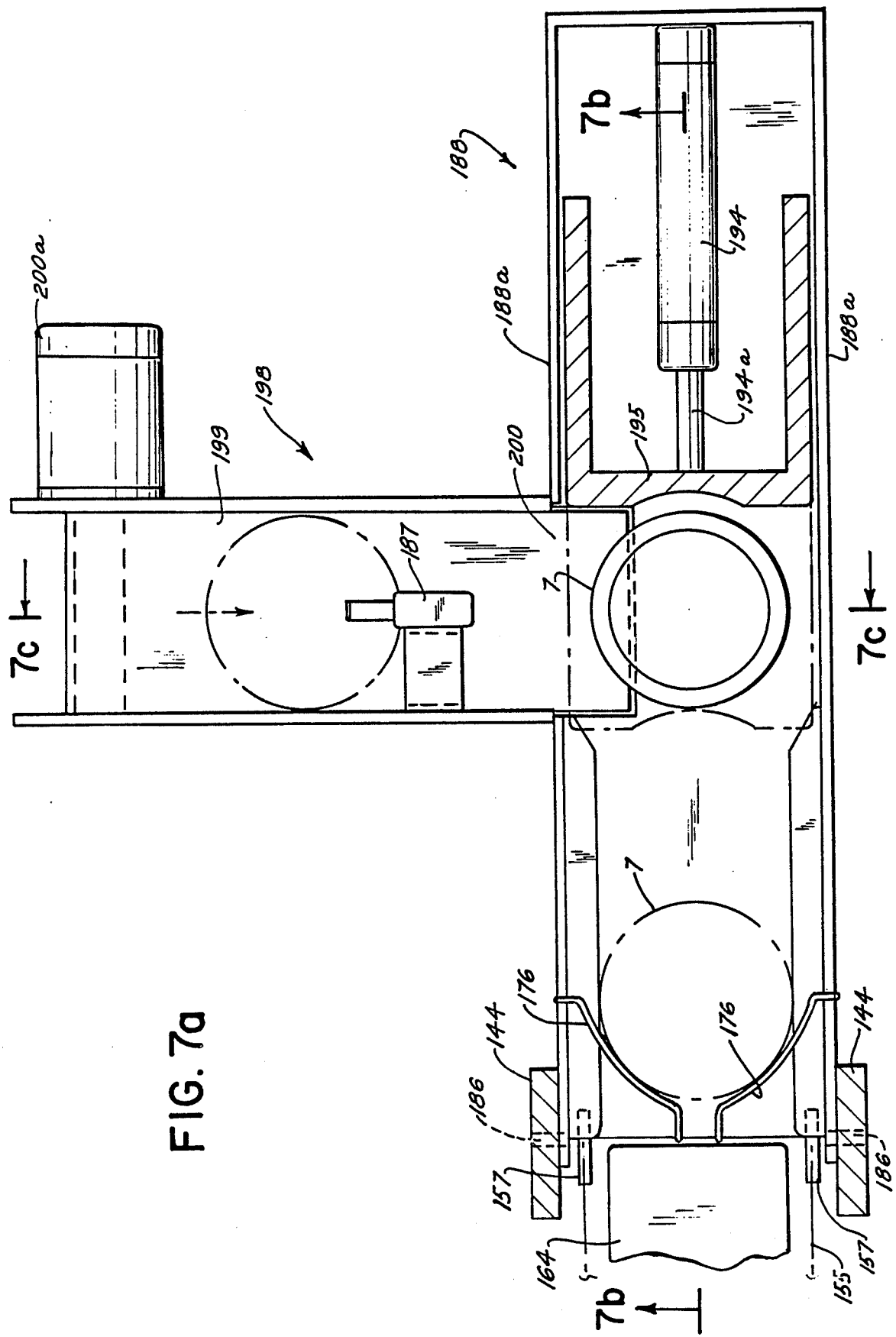

In combination with the same feed stacker bar 196, a can conveyor 198 may also be used. The can conveyor belt 199 advances a can 7 through the opening 200 in the channel wall 188a and with the feed head 195 in a position shown in FIG. 7a. The can 7 may then again be advanced one position forwardly in a machine direction into the top labeler section 13 by the cylinder head 195 or merely by the conveyor belt motion, depending on the weight and shape of the can 7.

A support leg 202, shown in FIG. 7, is also shown for the conveyor 198, serving also to support the can feed stacker 188.

Switch 199a is for the purpose of detecting the presence of a can 7. When a can is detected, it causes cylinder 194 to actuate and feed another can into the labeler. If no can is detected by switch 199a, cylinder 194 ceases to actuate until a can is detected.

Switch 187, which detects the presence or absence of a lid on the can, also functions as an additional quality control means.

Turning back to FIG. 5, it illustrates also the side label application section 49 which will now be briefly discussed in an introductory manner. From the conveyor chain 155 and the conveyor slide 164 the can 7 is deposited into the side label application section 49 onto the constantly rotating can rotation drive wheels 55. As shown in FIG. 4, these are being driven by an intertied pair of sprocket wheels 201 which are mounted on a pair of shafts 203. The shafts 203 are located in a mounting block 230. A drive sprocket wheel 207a, not shown in FIG. 5 but shown in FIG. 4 in connection with the schematic representation of the machine train, drives one of the shafts 203 as previously discussed in connection with FIG. 4.

In FIG. 5, the label press down roller gate disc 209 is shown in its engaged position, while in FIG. 8 it is shown in the uplifted position. The later position allows the can 7 to be dropped onto the continuously driven can rotation drive rollers 55. The label press down roller 57 has been shown in FIG. 5 to be in the engaged position on top of a can 7. As the can drops from the conveyor 155 with the press down roller gate disck 209 being in the open position, the can 7 is restrained from falling sideways out at the bottom by can alignment finger 226.

Thereafter the label press down roller 57 and label press down roller gate disk 209 are brought down onto the can, as it will be further discussed herein. The above description thus completes the description of the machine as it relates to the top label 9 placement on the can 7.

Turning now to FIG. 3, the side label application will now be discussed in conjunction with FIG. 3 and other related figures. As previously identified but for sake of recapitulation, the main machine base plate has been identified as 102; the main vertical frame member as 103, and the main horizontal frame member as 104. The housing for control means has been shown as 107, and bracket 105 identifies a bracket for the side label supply spool 25 and side label speed compensation wheels 27 and idler pullies 29, as well as the arrangement for the side label carrier strip 26 takeup spool 62.

A dance arm 251 for side label supply spool 25 pivots above the supply spool 25 on pivot point 252. A detent pin 253 for the side label dance arm 251 is mounted on bracket 105. A brake band 255 for side label supply spool 25 is around hub 256. On the outside of hub 256 is placed the side label supply spool 25. The brake band is attached to the dance arm 251 at hrake band anchor pin 257, and at the other end via spring 258 at the bracket anchor pin 259. Because a side label 24 represented by the circumference of a container is considerably longer, the dance arm 251 has been provided with two side label speed compensation wheels 27.

From the side label supply reel 25 and from the last idler pullies 29, the pre-feed pulley 31 guides the side label carrier 26 with the side labels 24 thereon into the tax stamp applicator section 30 feed wheel 33.

A pair of sensors 260 and 261 adjusted to read through the carrier 26 but not through the carrier and label 24 thereon sense the leading and trailing edge of the label and work as follows. Sensor 260 senses the leading edge of the side label and starts the glue applicator 35, pre-set to apply glue to the next label ahead. The sensor 261 detects the leading edge of the same side label 24 and stops the glue application on the preceding side label. However, the glue application is started only if the proper "tax stamp present" signal has been received on tax stamp pickup head 37.

The duration for the glue application (and hence the distance on the label) may be adjusted physically by the placement of the sensors on the sensor mount 263, as well as by electronic timing means. The sensors are carried on a device somewhat like a horseshoe type or a "C" ring type carrier (not specifically identified) with the label sliding in the opening on a carrier plate 104a mounted on top of the main horizontal beam 104.

An adjustable mounting arm 265 for the glue applicator 35 is on the main horizontal machine member 104. Thus the adjustment arm 265 allows an adjustment for the glue dots 266 (not shown in FIG. 3 but shown in FIGS. 9 and 10), placed crosswise on the side label. Lengthwise on the top of a side label an appropriate distance for glue deposition is adjusted by the sensors 261 and 260 and/or their associated timing circuits. The gluer consists of a pair of ball point pen-like glue heads 35a which may deposit a continuous strip or, as mentioned before, the dots 266. The gluer 35 and each of the heads are supplied by a conduit 36 from glue container 111. The gluer 35 is raised and lowered by a solenoid 267 (or a pneumatic cylinder) which can be precisely controlled by the previously discussed sensors 260 and 261 which sense the leading and trailing edge of the side label in relationship to the downstream labels. The gluer 35 may be programmed to deposit the necessary number of glue dots 266 for the necessary lenqth as dictated by the size of the stamp or the length thereof.

Tax stamps 28 are stored in a storage sleeve or storage magazine 270. Typically a stack of stamps are in the storage magazine 270. These are restrained on the bottom thereof by four small pins (not shown) which prevent the stack from descending downwardly.

The tax stamp deposit and pickup section 30 consists of a head for tax stamp pickup and deposit, shown as 37 in FIG. 2. The pneumatic cylinder 38 for raising the tax stamp head 37 in a position to pick up a tax stamp 28 from the magazine 270 is used also to deposit the tax stamp 28 as follows.

A crank arm 271 for the tax stamp pickup head 37 is shown as 271; the arm pivot is driven by a rack and pinion combination (pneumatically driven). The pivot point 273 is also the pinion shaft 273 for crank arm 271. The tax stamp pickup and deposit section 30 will be further described in detail in FIGS. 9, 10 and 11 in conjunction with the actual sequence of tax stamp pickup and deposition on the side label 24.

After the tax stamp 28 has been placed on the side label 24 and as part of the advancement, the tax stamp 28 is further trimmed to size, if necessary, in the tax stamp slitter section 39, again the details of which will be discussed in conjunction with FIGS. 10 to 12. For safety's sake, an appropriate shroud 286 is placed over the tax stamp slitter section 39. Shroud 286 may be of an appropriate material such as plexiglass and the like.

Figure 13:
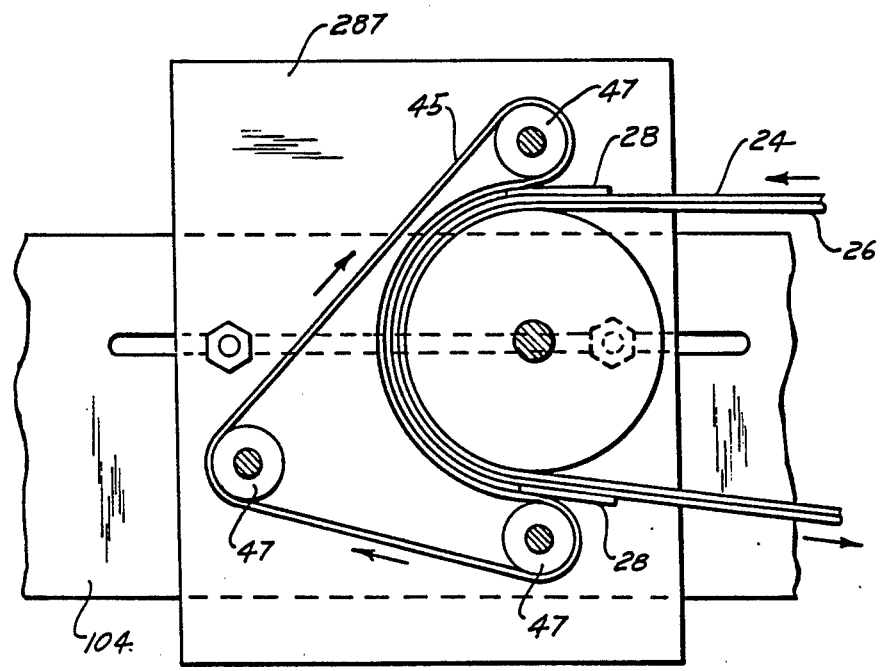
FIG. 13 illustrates in an enlarged side elevation the tax stamp hold down conveyor previously shown in FIG. 3.

A tax stamp hold down conveyor 45, shown also in FIG. 13, assures that the previously applied glue, if it has not set, does not allow the tax stamp to be dropped from the side label when the side label 24 and its carrier strip 26 reverse the direction around the tax stamp section take-off wheel 43. The press down belt conveyor 45 thus secures the tax stamp on the side label. The press down belt conveyor 45 is driven by the side label carrier strip 26 and is a continuous belt played around take-off wheel 43 by conveyor belt wheels 47, three of which have been employed for that purpose.

The previously described guide wheel 51 then leads the side label carrier strip 26 into the side label applicator section 49. A mounting bracket 290 holds a pair of sensors in the form of a horseshoe identified as 291 and 292. Sensor 292 detects the trailing edge of the following side label and stops the feeding of the labels by the drive roller 59.

Plate 125 with a right angle base has mounted thereon the sensor bracket 290, sensors 291 and 292, a tension equalizer roller 294 and a pair of posts 128 between which are placed the side label carrier drive wheel 59, its complementary take-off assist wheel 60 and stripper plate 53.

Sensor 291 detects the presence or absence of a tax stamp. By an appropriate mechanism which will be further described herein, after application of the side label free of a tax stamp (the second can), the can is ejected as an unacceptable item for subsequent application of a tax stamp or a second side label on top of the first label thereon. Tax stamp empty side label has no glue on it, because gluer 35 is engaged only after the tax stamp 28 has been picked up.

When the pneumatic cylinder 214 activated gate frame 210 has gone through an up position, the drive roller 59 is activated, and when the gate frame is brought down and sensor 292 senses the trailing edge of the preceding side label, the drive roller 59 is stopped.

Because of the unequal diameter of the can and the lid for the can, the tension equalizer roller 294 is also used to lift up the edge of the side label carrier strip 26 in such a manner as to equalize the tension on the entire carrier strip 26 in a cross-machine direction thereof. It has been found to be necessary because of tearing of the side label carrier strip 26. The uplifted edge is towards the viewer in FIG. 3, as is the can lid on a can in the applicator section 49. Thus, the pivot point 126 and pivot plate 125 (with posts 128 thereon) alter the entry of the side label 24 with its carrier strip relative to the can on can rotation drive rollers 55 from about one deqree to three degrees to assure proper placement on a container with a lid of a slightly larger diameter. The adjustment point for plate 125 has been identified as 127 and is a set screw, a bolt or a lock bolt and the like.

A bracket 295 for adjusting the tension equalizer roller 294 has been shown in FIG. 3.

Turning now to FIG. 8 and in conjunction therewith FIGS. 5 and 6, the label 24 with the tax stamp 28 thereon is shown in FIG. 8 as being advanced around the stripper plate 53. The can is precisely positioned by flanges 55a on the continuously rotating can rotation drive rollers 55 and by the press down roller 57, including the label press down roller gate disk 209. The carrier strip 26 driven roller wheel 59 and the carrier strip takeoff assist wheel 60 advance the side label carrier strip 26. That is, upon completion of the engagement of the can 7 with label press down roller 57 for one revolution (at a low pressure being exerted on the press down roller 57 by pneumatic cylinder 214 bearing down on the press down roller shaft 219), the label 24 is firmly and precisely attached to the diameter-wise wider portion of the can 7. Thereafter rotating a few additional times, e.g., two, depending on the appearance and the like by bearing down more heavily on the roller 57 in the second stage, a precise alignment of the side label 24 on can 7 is achieved.

The press down pneumatic cylinder 214 is yoked to the press down roller gate frame 210 and attached at the top of the frame to 210 by pivot togle plate 218 via a top pivot toggle 217. The press down roller gate frame 210 pivots around shaft 211. A bottom pivot toggle 216 for pneumatic cylinder 214 has also been shown in FIG. 6. Likewise a partial side view of the side label application section 49 is shown in FIG. 5.

In FIG. 8, the adjustment means have been illustrated for adjusting the precise side label 24 placement on a can 7 being driven by the rollers 55. The pivot point 126 in FIG. 2 allows the stripper plate 53 mounted on the plate 125 to be arcuately adjusted to compensate for the thickness of the lid diameter versus the can diameter for a can, as mentioned before. Typically plate 125 may be skewed by varying the angle of entry of the side label and its carrier strip, e.g., from about 1 to 4 degrees, but also depending on the difference for the lid diameter compared to the can diameter. The adjustment may then be secured such as by a locking arrangement, i.e., lock bolt 127, shown in FIG. 2.

A pair of proximity sensors 224 and 223 sense the position of a press down roller sensor plate 221 for determining the up and down position of press down roller gate frame 210. These sensors have been shown in FIG. 6, as well as in FIG. 8, with the press down roller sensor plate 221 being also illustrated in FIG. 8 in both the up and down positions.

After the side label 24 has been properly applied in the side label applicator section 49, a can 7 is then ejected. For illustrating this aspect of the invention, FIG. 5 shows a can eject pneumatic cylinder 229 having attached thereto a can eject piston rod 231 riding in a 230a for a can eject piston rod guide, shown in block 230 in FIG. 5. The can eject piston rod 231 has a piston head 232 which is placed between the can rotation drive rollers 55, further as illustrated in front elevation view in FIG. 3 and in FIG. 8 in an enlarged partial front elevation. Can rotation drive roller 55 shafts 203 are also placed in block 230.

As the can eject piston head 232 moves forward, a can alignment finger 226 pivoted on pivot point 227 gravitationally moves downwardly and the piston head then urges the can 7 at the bottom part thereof onto a finished product chute 233. It must be remembered that at that juncture the press down roller frame 210 is in the up position.

Upon retraction of the can eject piston rod head 232, the can alignment finger 226 is lifted back in the position as shown in FIG. 5.

In the event sensor 291 has detected an absence of a tax stamp, then a solenoid activated valve from a pneumatic line causes an air blast through nozzle 236, shown in FIG. 8, to eject a can from side label applicator section 49 to be ejected leftward as shown in FIG. 8 across the inclined surface 233. On the right of this inclined surface 233, also shown in FIGS. 5 and 6, are gravitationally discharged the acceptable cans. The inclined surface may be appropriately pivoted at pivot point 234 to accomodate the various weights of the cans before their ejection or to facilitate further packaging.

Figure 9:
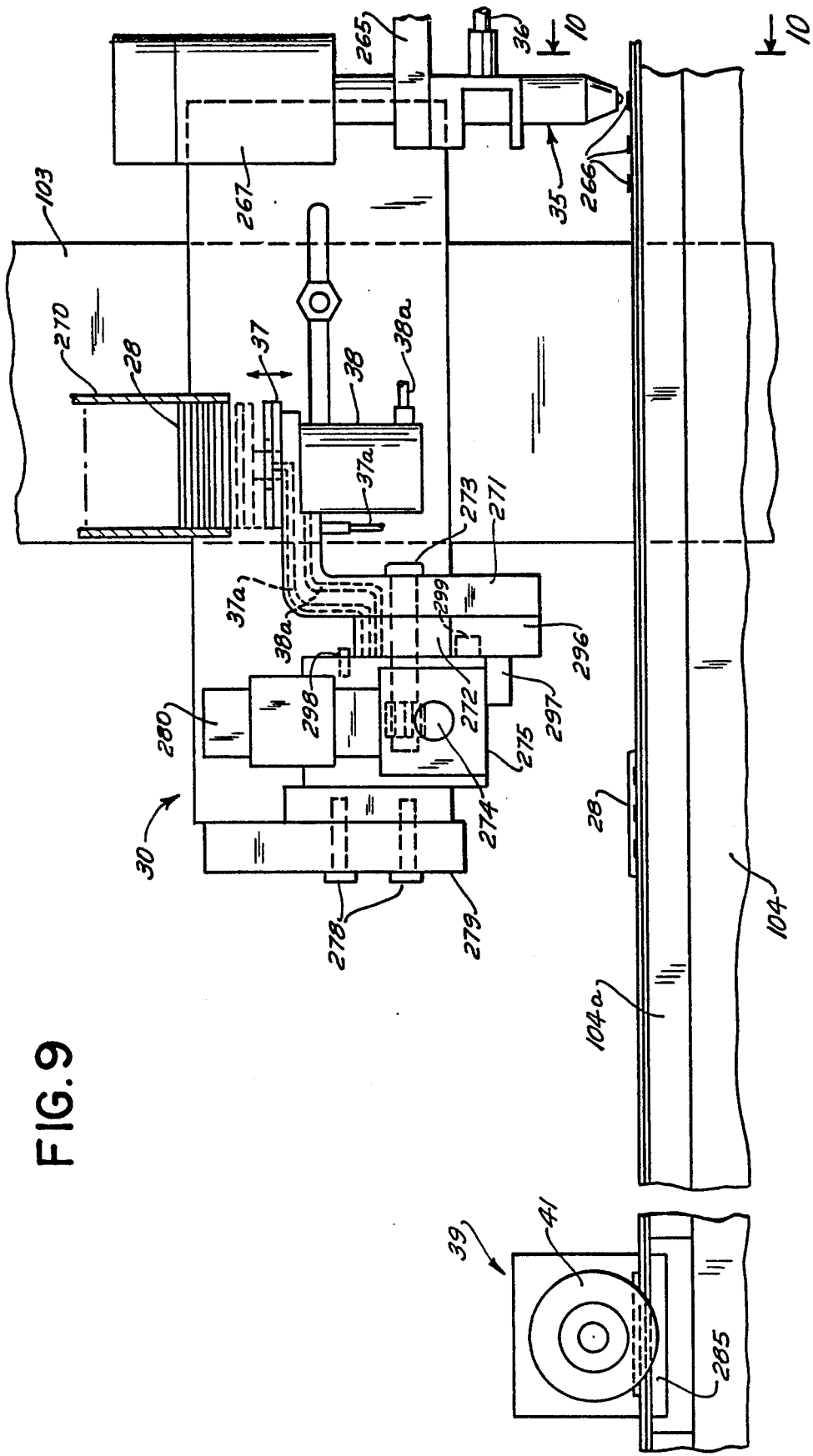
FIG. 9 is an enlarged, partial side elevation of a glue applicator and tax stamp deposition means, including a tax stamp slitter.
Figure 11:
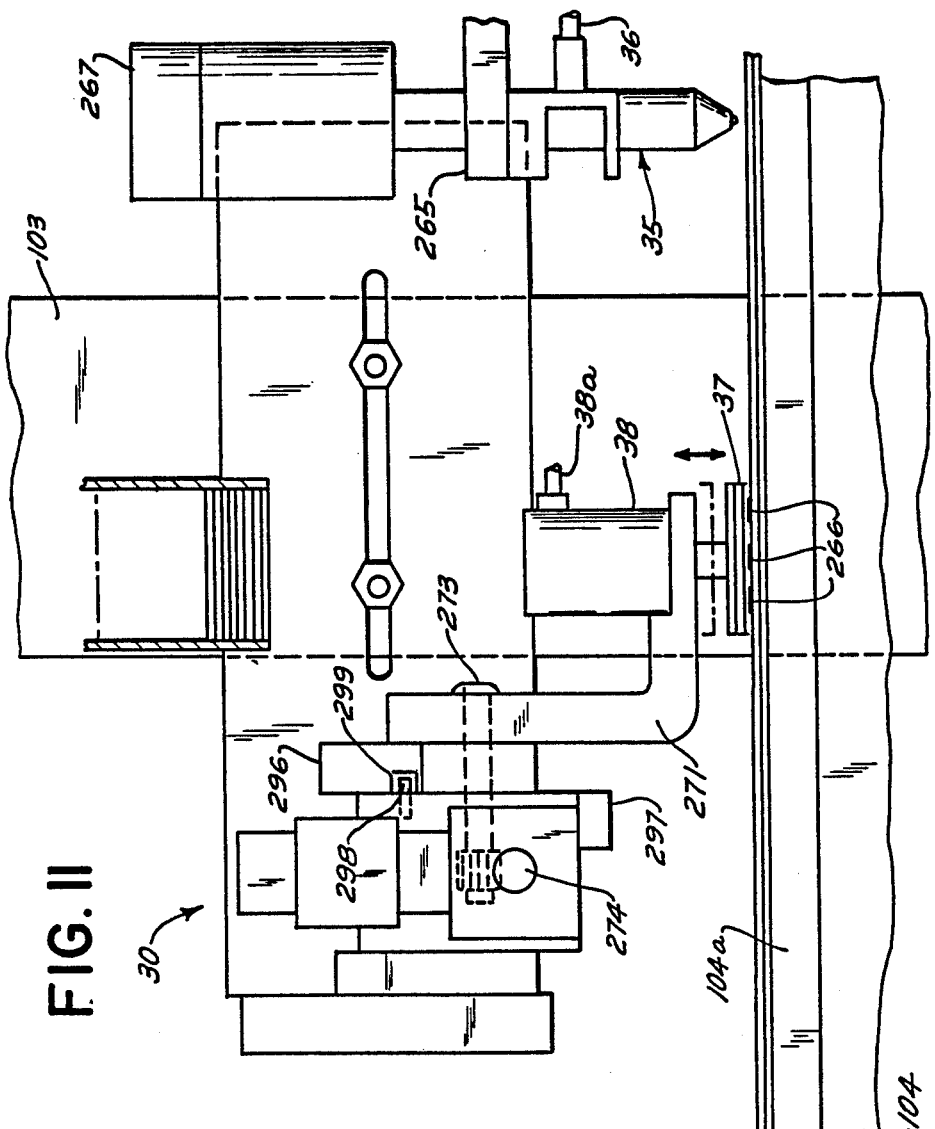
FIG. 11 is an enlarged partial side elevation of a tax stamp placement on the side label.
Figure 10:
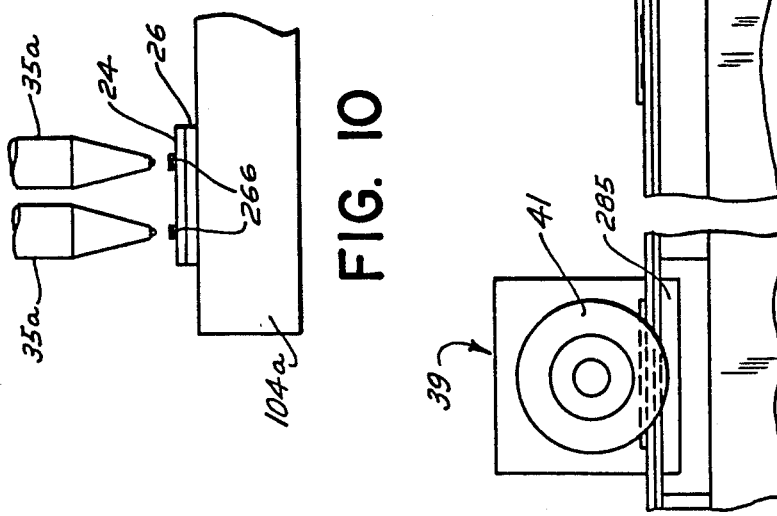
FIG. 10 is a partial cross-section along lines 10—10 of FIG. 9.

Turning now to FIGS. 9 to 11 which illustrate in greater detail the tax stamp application section 30, in FIG. 9 the crank arm 271 for tax stamp pickup head 37 has been shown in its up position, that is, in the position where the stamp pick-up head 37 picks up a stamp 28 from a stamp magazine 270. The tax stamp pickup head has a pneumatic and vacuum connection 37a which has been identified schematically, but which is housed along with the pneumatic connection 38a for the pneumatic tax stamp pickup and deposit pneumatic cylinder 38 in the crank arm 271. The connections may also be by appropriately reinforced hoses (not shown).

The passage for the joint vacuum and pressure has been identified as 37a, and the passage for the pneumatic high pressure air to cylinder 38 has been identified as 38a. In its up position, the pneumatic cylinder 38 extends the head 37, at which time an appropriate vacuum in line 37a draws one of the stamps away from the magazine 270. If an appropriate vacuum setting is not registered in the tax stamp pickup head 37, it either indicates a failure to pick up a tax stamp, or if a repeated failure to pick up a tax stamp is shown, the machine is stopped and a "tax stamp empty" magazine is signaled to an operator.

The vacuum line 37a thus also acts as a safety-design feature to assure the proper tax stamp deposition on the side label 24.

After the tax stamp 28 has been picked up, the crank arm 271 is rotated around its pinion shaft 273. The pinion shaft 273 is driven by rack 274 in a reciprocal manner (i.e., rack 274 is a two-way, pneumatically driven rack).

A rotating plate 296 which rotates with the crank arm 271 serves to signal the crank arm 271 to be in the up position when sensor 297 senses the presence of the plate and in the down position when sensor 298 senses crank arm 271 to be in the down position. Notch 299 in rotating plate 296 covers up sensor 298 when the crank arm 271 is in the down position. Other sensing arrangements may also be shown.

The sensing is further shown in FIG. 11 when the rotating plate 296 is rotating with the crank arm 271.

The rack 274 for pinion shaft 273 is housed in a rack housing 275. Adjustment means for crank arm 271 have been illustrated as 278, and a bracket 279 has also been provided for crank arm 271. A pneumatic flow control valve 280 acts as a brake arrangement for the pneumatically driven rack 274 to prevent excessive shock loading of crank arm 271 as it is rotated from the up to the down position or vice-versa.

In order to assure that the stamp 28 is positively deposited on the side label in the "deposit" position shown in FIG. 11, the vacuum which previously has been present in the pickup head 37 is now replaced with a slight overpressure in conduit 37a, as it will be further discussed herein in connection with the control means, and the positive release of the stamp 28 is thus assured. Vacuum switch valve 311 shown in FIG. 2 governs that operation. The stamp 28 which has now been deposited on the side label then travels on to the tax stamp slitter section 39 where the rapidly rotating knives 41, typically made of a suitable sintered carbide material, slit the overhanging edges of the tax stamp, as further illustrated in FIG. 12.

Figure 12:
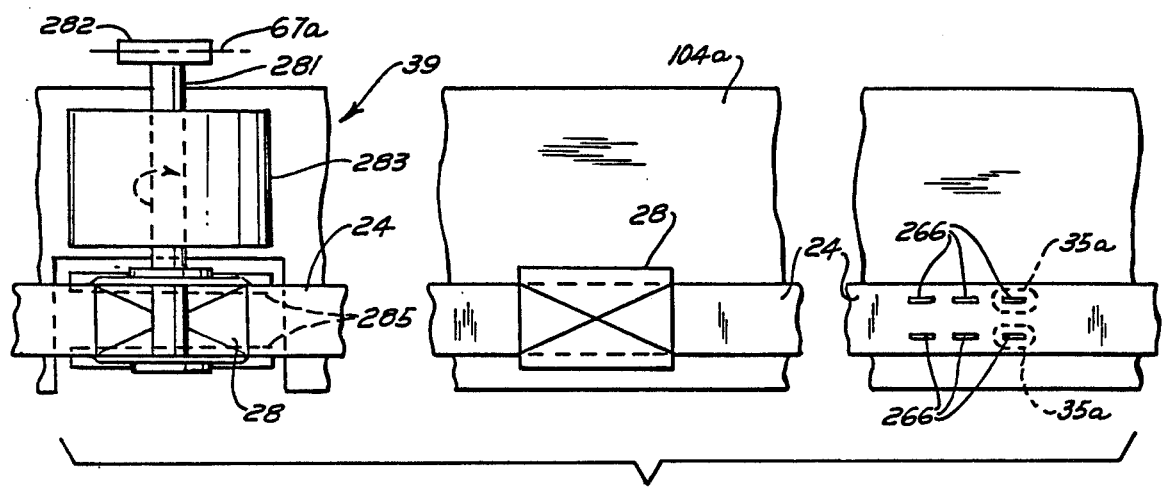
FIG. 12 illustrates schematically the top view of the glue placement, the tax stamp placement, and the tax stamp slitter section previously shown in FIG. 11.

The knives 41 work against a hardened tool steel insert 285 shown in front elevation in FIG. 11 and in a top view in FIG. 12. A shaft 281 for knives 41 is driven by a pulley 282 for belt 67a, previously discussed in connection with FIG. 4. Shaft bushing 283 maintains the slitter knives 41 in a true alignment and assures very precise tax stamp cutoff.

In FIG. 13, an adjustment plate 287 has been shown for the hold down conveyor which assures that the tax stamp 28 stays on the label and is not removed, and also providing an ample opportunity for the glue to set.

Turning now to FIG. 3, it illustrates the solenoid valves which are used for controlling the various pneumatic cylinders and pneumatic means used for operating the present machine. Thus the topmost solenoid identified as 301 is for low pressure air regulation. Low pressure air is used in pneumatic cylinder 214 for the side label applicator section 49 when the press down roller 57 engages the can at the lid part thereof.

After a complete rotation of the can without the label being askewingly attached to the can, the air pressure is increased to about 400% to achieve the further and complete label attachment to the can. The solenoid valve 302 switches from the low pressure to the high pressure cylinder 214. Solenoid valve 303 is for the pneumatic cylinder 214 with a gate 209 being in the up or down position.

Solenoid valve 304 is for pneumatic cylinder 229 shown in FIG. 5 for ejecting can 7 after labeling has been completed. Solenoid valve 305 is for rejecting improperly labeled cans by means of an air blast at 236.

Solenoid valve 306 is for pneumatic cylinder 182 for lifting bridge 181. Solenoid valve 307 is for pneumatically driven rack 274 which rotates crank arm 271 from the pickup to the deposit location and return. Solenoid valve 308 is for pneumatic cylinder 38 which picks up and deposits a tax stamp 28. It is a two position solenoid valve.

Solenoid valve 309 is for controlling high pressure which is for all pneumatic circuits except for pneumatic cylinder 214 which is operated at both low and high pressure as previously explained.

Gauge 310 shows vacuum in line 37a during pickup cycle for the pickup head 37.

Vacuum switch valve 311, shown in FIG. 2, shows a vacuum condition, a pressure on condition, or neither condition, for the vacuum-pressure line 37a as previously discussed, and thus signals appropriate or inappropriate conditions as the case may be.

Gauge 312, also shown in FIG. 2, is the low pressure gauge, while gauge 313 shows high pressure.

Figure 14:
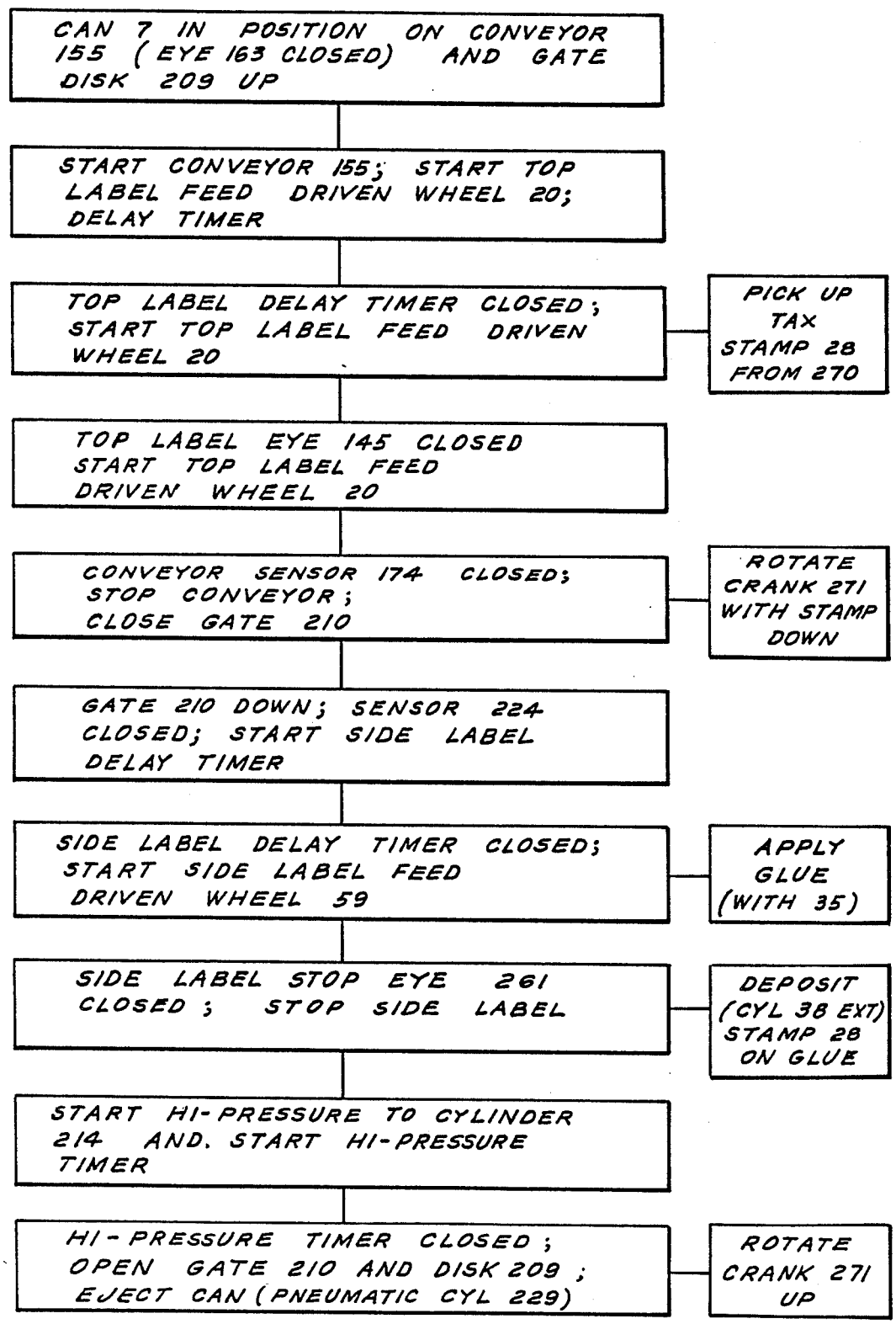
FIG. 14 illustrates the automatic operation of the machine in a block diagram form, including the independently operable tax stamp section.

Turning now to FIG. 14, it illustrates schematically in the lefthand column the automatic operation without the tax stamp section 30 being on, and on the right hand column the block diagram with the tax stamp section 30 being on and interconnected with the automatic operation of the machine.

The sequence is illustrated in the block diagram by reference to the various sensor conditions or control positions and is readily understandable by the legends in each of the blocks.

The electronic or electrical control elements which have not been specifically identified are housed in control housing 107 for the machine. A control device such as for the various sensing, delay or timing circuits is available from Siemens-Allis, P.O. Box 9128, Waltham, Mass., 02254, and may be readily externally programmed for the various control functions. One such programmable control device is sold under the trademark SIMATICS 5101R and is available from the above source. Similarly, the various relays and solenoid valves used in connection therewith are readily available on the market.

From the above description and the description of the specific embodiment, it can easily be seen that machines for processing containers of various diameter to height ratios may be adapted based on the disclosure of this application. Consequently, the benefits which are gained by the presently described machine may be utilized for improving the label appearance as well as label application rates for a number of cans. Still further, a side label may be modified for including additional information on the side label, such as tax stamps; product information; controlled substance information; pricing information; quality control information; if licensed, licensing information; manufacturing source information; customs information and the like.

Because of the very precisely controllable locations for applying a label on a can such as a top label and the very precise adjustments in the location, such as to within a few thousands of an inch, e.g., from 0.001 to 0.005, the product appearance and quality is considerably enhanced and the product integrity assurance is substantially unquestionable.

Still further, the ability to invert a can and refeed the can by precisely positioning on the bottom thereof an additional label is also possible such as by the means shown in FIGS. 7 to 7c, all at the same time while the side labeling operation of the machine has been disabled.

Still further, for side label applications where no additional labeling information is needed, that is, where no tax stamp and the like need be placed on the label, section 30 of the machine may likewise be disabled. Similarly, by keeping the gate frame 210, as shown in FIG. 8, in the up position, thereby not advancing the side label by the drive roller 59, the side label application may be disabled.

As a result, the extreme versatility of the machine now allows considerable manufacturing independence and prevents manufacturing vulnerability associated with prior art labeling machines which were single product dedicated or entire production dedicated. At the same time, extremely good quality control is assured for all products coming off the machine.

While the above machine has been described with respect to the embodiments shown in the figures and illustrated by the method by which the labels have been applied, the scope of the invention is not to be limited by the above description, but is to be considered in light of the appended claims.

What is claimed herein:

1. A method for labeling a container such as a can and the like a top or bottom label and a side label, comprising the steps of:
    (a) feeding a container into a top or bottom labeling station;
    (b) advancing synchronously a chain conveyor with a container thereon and a label carrier strip;
    (c) applying said top or bottom label on said container as said chain conveyor and said label carrier strip are being driven;
    (d) interrupting the driving of said label carrier strip while said conveyor is being driven;
    (e) admitting to a side positioning zone a container which has been top or bottom labeled while said conveyor is being driven;
    (f) positioning on a side said container;
    (g) feeding a side label into said positioning zone;
    (h) rotating said container on a side; and
    (i) joining said rotating container with said side label under stagewise increased pressure on said side label.

2. The method as defined in claim 1, wherein said method includes gluing a tax stamp on said side label and feeding a side label with said tax stamp thereon and joining said rotating container with said side label with said tax stamp thereon.

* * * * *